United States Patent
Glorius et al.

(10) Patent No.: US 8,912,342 B2
(45) Date of Patent: *Dec. 16, 2014

(54) PYRAZOLE SYNTHESIS BY COUPLING OF CARBOXYLIC ACID DERIVATIVES AND ENAMINES

(71) Applicant: Westfaelische Wilhelms Universitaet Muenster, Muenster (DE)

(72) Inventors: Frank Glorius, Ascheberg (DE); Mamta Suri, Muenster (DE)

(73) Assignee: Westfälische Wilhelms Universität Münster (DE)

( * ) Notice: Subject to any disclaimer, the term of this patent is extended or adjusted under 35 U.S.C. 154(b) by 69 days.

This patent is subject to a terminal disclaimer.

(21) Appl. No.: 13/759,107

(22) Filed: Feb. 5, 2013

(65) Prior Publication Data
US 2013/0204011 A1 Aug. 8, 2013

(30) Foreign Application Priority Data
Feb. 6, 2012 (DE) .......................... 10 2012 100 961

(51) Int. Cl.
C07D 231/12 (2006.01)
C07D 231/14 (2006.01)
C07D 405/04 (2006.01)

(52) U.S. Cl.
CPC ............ *C07D 231/14* (2013.01); *C07D 405/04* (2013.01); *C07D 231/12* (2013.01)

USPC ..................................... 548/365.7; 548/374.1

(58) Field of Classification Search
CPC ... C07D 231/12; C07D 231/14; C07D 405/04
USPC .......................................... 548/365.7, 374.1
See application file for complete search history.

(56) References Cited

U.S. PATENT DOCUMENTS 8,716,485 B2 5/2014 Neumann et al.
2013/0012715 A1 1/2013 Neumann et al.

FOREIGN PATENT DOCUMENTS

DE 102010013 282 A1 9/2011

OTHER PUBLICATIONS

Neumann, et al., "Effiziente Pyrazolsynthese durch eine oxidative C-C/N-N-Bindungsknüpfungskaskade" Angew. Chem. 2010, 122, 7957-7961. 6 pages.
Application No. EP 13 15 4273, European Search Report dated Sep. 25, 2013. 3 pages.

*Primary Examiner* — Kamal Saeed
(74) *Attorney, Agent, or Firm* — Schmeiser, Olsen & Watts, LLP

(57) ABSTRACT

A method of synthesizing Pyrazoles by means of the oxidative conversion of Enamines with suitable N-containing carboxylic acid derivatives in the presence of copper ions and 2-picolinic acid derivatives is provided.

5 Claims, No Drawings

PYRAZOLE SYNTHESIS BY COUPLING OF CARBOXYLIC ACID DERIVATIVES AND ENAMINES

FIELD OF TECHNOLOGY

The following relates to the field of organic synthesis, especially the field of heterocycle synthesis.

BACKGROUND

Heterocyclic compounds play an immense role in organic chemistry, especially in active ingredients and pharmaceuticals, and the synthesis of heterocyclic compounds represents an important and steadily growing field of research.

Pyrazoles represent an important class of heterocycles. Pyrazoles occur relatively rarely in natural materials but are an important structural element in biologically active compounds, which in some cases can have great economic importance as pharmaceuticals or plant protecting agents. Two prominent examples are the COX-2 inhibitor Celecoxib, which is used to treat rheumatoid arthritis, and the contact poison Fipronil®, which is effective as a GABA inhibitor against ectoparasites, such as fleas, lice, ticks, and mites.

A Pyrazole-synthesizing process using the coupling of carboxylic acid derivatives and Enamines under oxidative conditions is known from WO 2011/120861. However, the task at hand is to improve this method further.

SUMMARY

This task is accomplished by means of a method according to claim 1. It proposes a method of making Pyrazoles by the conversion of Enamines and carboxylic acid derivatives in the presence of an oxidizing agent. Copper ions and 2-picolinic acid (derivatives) are proposed.

Surprisingly, it was shown that under these conditions the yields could usually be substantially increased compared to the methods known in the prior art.

The term "conversion" in the sense of the present invention means, in particular, that the respective substrate is brought into contact with itself and the other reactants. As a rule, this takes place through mixing or suspending. It should be noted that depending on the actual implementation of the method, either the two educts are presented and then oxidized; however it can also be advantageous to present one reactant together with the oxidizing agent, and then to add the other educt.

According to one preferred embodiment of the invention, the reaction temperature lies between ≥0 and ≤200° C., preferably between ≥60 and ≤140° C., and quite particularly between ≥80 and ≤120° C.

Neither the pressure nor the type of gas atmosphere over the reaction is critical, and different gases and pressures are suitable, for example, air, nitrogen, argon, oxygen; preferably air and nitrogen. The reaction can be carried out at different pressures, preferably at pressures of 1 to 10 atm, and quite particularly at 1 to 4 atm. Increasing the pressure can lead to an increase of the boiling point, which can cause an acceleration of the reaction.

Another object of the invention is any process in which the reaction product continues to react under the reaction conditions or due to gradual variation of the reaction conditions, for example, by means of saponification of an ester group, a decarboxylation reaction, or a hydration.

The preparation of the reaction mixture and purification of the products are usually less critical and are governed according to the corresponding physical properties of the products and byproducts that are generated. Preferred methods for preparation and purification are distillation, sublimation, crystallization, chromatography, filtration, and extraction. Because hydrazines are avoided, purification is generally simpler compared to the previous purification processes and it is possible to obtain a product with a greater purity.

DETAILED DESCRIPTION

According to one preferred embodiment of the invention, the ratio of Enamines to N-containing carboxylic acid derivatives (mol of N-containing carboxylic acid derivatives to mol of Enamine) is 0.2:1 to ≤150:1, preferably ≤1:1 to ≤100:1, and most preferably ≤2:1 to ≤20:1. The excess of N-containing carboxylic acid derivative can come about, for instance, by the reaction taking place in the N-containing carboxylic acid derivative as solvent. Preferred compounds in this case are especially acetonitrile, propionitrile, isobutyronitrile, butyronitrile, valeronitrile, capronitrile, heptanoic acid nitrile, octanoic acid nitrile, nonanoic acid nitrile, benzonitrile, as well as their monofluorinated or polyfluorinated straight-chain and branched derivatives.

According to one preferred embodiment of the invention, the reaction takes place in a solvent selected from the group comprising pentane, hexane, heptane, octane, petroleum ether, toluene, xylenes, chlorobenzene, o-dichlorobenzene, ethyl acetate, tetrahydrofuran, diethyl ether, methyl tert-butyl ether, 1,4-dioxane, N,N-dimethyl formamide, dimethyl sulfoxide, 1,2-dichloroethane, N,N-dimethyl acetamide, dimethoxyethane, or carboxylic acids such as formic acid, acetic acid, trifluoroacetic acid, chloroacetic acid, trichloroacetic acid, propionic acid, butyric acid, or alcohols such as methanol, ethanol, propanol, isopropanol, butanol, t-butanol or phenol, preferably ethyl acetate, tetrahydrofurane, diethyl ether, methyl tert-butyl ether, 1,4-dioxane, N,N-dimethyl formamide, dimethyl sulfoxide, 1,2-dichloroethane, N,N-dimethyl acetamide, t-butanol, chlorobenzene, toluene, dimethoxyethane, hexane, o-dichlorobenzene, most preferably 1,4-dioxane, N,N-dimethyl formamide, dimethyl sulfoxide, 1,2-dichloroethane, N,N-dimethyl acetamide, t-butanol, and chlorobenzene, or mixtures thereof.

According to one preferred embodiment of the invention, the N-containing carboxylic acid derivatives are selected from the group comprising nitriles, carboxylic acid amides, amidines, imidates, imidoyl chlorides, derived protonated salts of these compounds, as well as mixtures thereof.

Compounds having the following structure are preferably used as Enamine s:

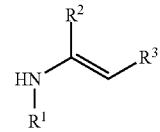

wherein $R^1$, $R^2$, and $R^3$ are selected, independently from one another, from the group comprising hydrogen, hydroxyl, halogen, pseudo-halogen, formyl, carboxyl and/or carbonyl derivatives, alkyl, long-chain alkyl, alkoxy, long-chain alkoxy, cycloalkyl, halogen alkyl, aryl, arylenes, halogen aryl, heteroaryl, heteroarylenes, heterocycloalkylenes, heterocycloalkyl, halogen heteroaryl, alkenyl, halogen alkenyl, alkinyl, halogen alkinyl, keto, ketoaryl, halogen ketoaryl, ketoheteroaryl, ketoalkyl, halogen ketoalkyl, ketoalkenyl, halogen ketoalkenyl, phosphoalkyl, phosphonates, phosphates, phosphine, phosphine oxide, phosphoryl, phosphoaryl, sulfonyl, sulfoalkyl, sulfoarenyl, sulfonates, sulfates, sulfones, amines, polyether, silyl alkyl, silyl alkyloxy, wherein one or more of the non-neighboring CH₂ groups can be substituted, independently from one another, by means of —O—, —S—, —NH—, —NR°—, —SiR°R°°—, —CO—, —COO—, —OCO—, —OCO—O—, —SO₂—, —S—CO—, —CO—S—, —CY1=CY2, or —C≡C— in suitable radicals, and specifically in such a way that the O and/or S atoms are not directly bonded to each other and are likewise optionally substituted with aryl or heteroaryl preferably containing 1 to 30 C atoms (terminal CH₃ groups are understood as CH₂ groups in the sense of CH₂—H).

Compounds having the following structure are preferably used as N-containing carboxylic acid derivatives:

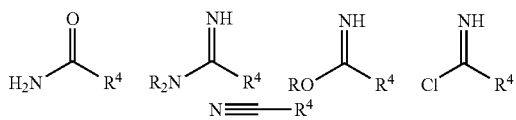

wherein R is selected from among alkyl, aryl, and halogen alkyl, and R⁴ is selected from the group comprising hydrogen, hydroxyl, halogen, pseudo-halogen, formyl, carboxyl and/or carbonyl derivatives, alkyl, long-chain alkyl, alkoxy, long-chain alkoxy, cycloalkyl, halogen alkyl, aryl, arylenes, halogen aryl, heteroaryl, heteroarylenes, heterocycloalkylenes, heterocycloalkyl, halogen heteroaryl, alkenyl, halogen alkenyl, alkinyl, halogen alkinyl, keto, ketoaryl, halogen ketoaryl, ketoheteroaryl, ketoalkyl, halogen ketoalkyl, ketoalkenyl, halogen ketoalkenyl, phosphoalkyl, phosphonates, phosphates, phosphine, phosphine oxide, phosphoryl, phosphoaryl, sulfonyl, sulfoalkyl, sulfoarenyl, sulfonates, sulfates, sulfones, amines, polyether, silylalkyl, silylalkyloxy, wherein one or several of the non-neighboring CH₂ groups can be substituted, independently from one another, by means of —O—, —S—, —NH—, -Nr°-, —SiR°R°°—, —CO—, —COO—, —OCO—, —OCO—O—, —SO₂—, —S—CO—, —CO—S—, —CY1=CY2, or —C≡C— in suitable radicals, and specifically in such a way that the O and/or S atoms are not directly bonded to each other and are likewise optionally substituted with aryl or heteroaryl preferably containing 1 to 30 C atoms (terminal CH₃ groups are understood as CH₂ groups in the sense of CH₂—H).

General Group Definition: In the description and the claims, general groups, such as for example: alkyl, alkoxy, aryl, etc., are claimed and described. Unless otherwise described, the following groups within the generally described groups are preferably utilized within the scope of the invention:
Alkyl: linear and branched C1-C8 alkyls.
Long-chain alkyls: linear and branched C5-C20 alkyls
Alkenyl: C2-C6 alkenyl.
Cycloalkyl: C3-C8 cycloalkyl.
Alkoxy: C1-C6 alkoxy.
Long-chain alkoxy: linear and branched C5-C20 alkoxy.
Alkylenes: selected from the group comprising: methylenes; 1,1-ethylene; 1,2-ethylene; 1,1-propylidene; 1,2-propylene; 1,3-propylene; 2,2-propylidene; butane-2-ol-1,4-diyl; propane-2-ol-1,3-diyl; 1,4-butylene; cyclohexane-1,1-diyl; cyclohexane-1,2-diyl; cyclohexane-1,3-diyl; cyclohexane-1,4-diyl; cyclopentane-1,1-diyl; cyclopentane-1,2-diyl; and cyclopentane-1,3-diyl.

Aryl: selected from aromatic compounds with a molecular weight of less than 300 Da.
Arylenes: selected from the group comprising: 1,2-phenylene; 1,3-phenylene; 1,4-phenylene; 1,2-naphthalenylene; 1,3-naphthalenylene; 1,4-napthalenylene; 2,3-naphthalenylene; 1-hydroxy-2,3-phenylene; 1-hydroxy-2,4-phenylene; 1-hydroxy-2,5-phenylene; and 1-hydroxy-2,6-phenylene.
Heteroaryl: selected from the group comprising: pyridinyl; pyrimidinyl; pyrazinyl; triazolyl; pyridazinyl; 1,3,5-triazinyl; quinonyl; isoquinoninyl; quinoxalinyl; imidazolyl; pyrazolyl; benzimidazolyl; thiazolyl; oxazolidinyl; pyrrolyl; thiophenyl; carbazolyl; indolyl; and isoindolyl, wherein the heteroaryl can be bonded to the compound via each atom in the ring of the selected heteroaryl.
Heteroarylenes: selected from the group comprising: pyridindiyl; quinolindiyl; pyrazodiyl; pyrazoldiyl; triazolediyl; pyrazindiyl; thiophendiyl; and imidazolediyl, wherein the heteroarylene functions as a bridge in the compound via a random atom in the ring of the selected heteroaryl, among which are especially preferred: pyridine-2,3-diyl; pyridine-2,4-diyl; pyridine-2,5-diyl; pyridine-2,6-diyl; pyridine-3,4-diyl; pyridine-3,5-diyl; quinoline-2,3-diyl; quinoline-2,4-diyl; quinoline-2,8-diyl; isoquinoline-1,3-diyl; isoquinoline-1,4-diyl; Pyrazole-1,3-diyl; Pyrazole-3,5-diyl; triazole-3,5-diyl; triazole-1,3-diyl; pyrazine-2,5-diyl; and imidazole-2,4-diyl; thiophene-2,5-diyl; thiophene-3,5-diyl; a —C1-C6-heterocycloalkyl selected from the group comprising: piperidinyl; piperidines; 1,4-piperazines, tetrahydrothiophenes; tetrahydrofurane; 1,4,7-triazacyclononanes; 1,4,8,11-tetraazacyclotetradecanes; 1,4,7,10,13-pentaazacyclopentadecanes; 1,4-diaza-7-thiacyclononanes; 1,4-diaza-7-oxacyclononanes; 1,4,7,10-tetraazacyclododecanes; 1,4-dioxanes; 1,4,7-trithiacyclononanes; pyrrolidines; and tetrahydropyran, wherein the heteroaryl can be bonded to the C1-C6 alkyl via any atom in the ring of the selected heteroaryl.
Heterocycloalkylenes: selected from the group comprising: piperidine-1,2-ylenes; piperidine-2,6-ylenes; piperidine-4,4-ylidenes; 1,4-piperazine-1,4-ylenes; 1,4-piperazine-2,3-ylenes; 1,4-piperazine-2,5-ylenes; 1,4-piperazine-2,6-ylenes; 1,4-piperazine-1,2-ylenes; 1,4-piperazine-1,3-ylenes; 1,4-piperazine-1,4-ylenes; tetrahydrothiophene-2,5-ylenes; tetrahydrothiophene-3,4-ylenes; tetrahydrothiophene-2,3-ylenes; tetrahydrofurane-2,5-ylenes; tetrahydrofurane-3,4-ylenes; tetrahydrofurane-2,3-ylenes; pyrrolidine-2,5-ylenes; pyrrolidine-3,4-ylenes; pyrrolidine-2,3-ylenes; pyrrolidine-1,2-ylenes; pyrrolidine-1,3-ylenes; pyrrolidine-2,2-ylidenes; 1,4,7-triazacyclononane-1,4-ylenes; 1,4,7-triazacyclononane-2,3-ylenes; 1,4,7-triazacyclononane-2,9-ylenes; 1,4,7-triazacyclonon-3,8-ylenes; 1,4,7-triazacyclononane-2,2-ylidenes; 1,4,8,11-tetraazacyclotetradec-1,4-ylenes; 1,4,8,11-tetraazacyclotetradec-1,8-ylenes; 1,4,8,11-tetraazacyclotetradec-2,3-ylenes; 1,4,8,11-tetraazacyclotetradec-2,5-ylenes; 1,4,8,11-tetraazacyclotetradec-1,2-ylenes; 1,4,8,11-tetraazacyclotetradec-2,2-ylidenes; 1,4,7,10-tetraazacyclododec-1,4-ylenes; 1,4,7,10-tetraazacyclododec-1,7-ylenes; 1,4,7,10-tetraazacyclododec-1,2-ylenes; 1,4,7,10-tetraazacyclododec-2,3-ylenes; 1,4,7,10-tetraazacyclododec-2,2-ylidenes; 1,4,7,10,13 pentaazacyclopentadec-1,4-ylenes; 1,4,7,10,13-pentaazacyclopentadec-1,7-ylenes; 1,4,7,10,13-pentaazacyclopentadec-2,3-ylenes; 1,4,7,10,13-pentaazacyclopentadec-1,2-ylenes; 1,4,7,10,13-pentaazacyclopentadec-2,2-ylidenes;

1,4-diaza-7-thiacyclononane-1,4-ylenes; 1,4-diaza-7-thiacyclononane-1,2-ylenes; 1,4-diaza-7-thiacyclononane-2,3-ylenes; 1,4-diaza-7-thiacyclononane-6,8-ylenes; 1,4-diaza-7-thiacyclononane-2,2-ylidenes; 1,4-diaza-7-oxacyclononane-1,4-ylenes; 1,4-diaza-7-oxacyclononane-1,2-ylenes; 1,4-diaza-7-oxacyclononane-2,3-ylenes; 1,4-diaza-7-oxacyclononane-6,8-ylenes; 1,4-diaza-7-oxacyclononane-2,2-ylidenes; 1,4-dioxane-2,3-ylenes; 1,4-dioxane-2,6-ylenes; 1,4-dioxane-2,2-ylidenes; tetrahydropyran-2,3-ylenes; tetrahydropyran-2,6-ylenes; tetrahydropyran-2,5-ylene; tetrahydropyran-2,2-ylidenes; 1,4,7-trithiacyclononane-2,3-ylenes; 1,4,7-trithiacyclononane-2,9-ylenes; and 1,4,7-trithiacyclononane-2,2-ylidenes, Heterocycloalkyl: selected from the group comprising: pyrrolinyl; pyrrolidinyl; morpholinyl; piperidinyl; piperazinyl; hexamethylene imines; 1,4-piperazinyl; tetrahydrothiophenyl; tetrahydrofuranyl; 1,4,7-triazacyclononanyl; 1,4,8,11-tetraazacyclotetradecanyl; 1,4,7,10,13-pentaazacyclopentadecanyl; 1,4-diaza-7-thiacyclononanyl; 1,4-diaza-7-oxacyclononanyl; 1,4,7,10-tetraazacyclododecanyl; 1,4-dioxanyl; 1,4,7-trithiacyclononanyl; tetrahydropyranyl; and oxazolidinyl, wherein the heterocycloalkyl can be bonded to the compound via any atom in the ring of the selected heterocycloalkyl.

Amines: the group —N(R)2, wherein each R is independently selected from among: hydrogen; C1-C6 alkyl; C1-C6 alkyl-C6H5; and phenyl, wherein if both R' are C1-C6 alkyl, then both R' can form an —NC3 to NC5 heterocyclic ring, wherein the remaining alkyl chain forms an alkyl substituent on the heterocyclic ring.

Halogen: selected from the group comprising: F; Cl; Br and I.

Halogen alkyl: selected from the group comprising monohalogenated, dihalogenated, trihalogenated, polyhydrogenated, and perhalogenated linear and branched C1-C8 alkyl.

Pseudo-halogen: selected from the group comprising: —CH, —SCN, —OCN, N3, —CNO, —SeCN.

Sulfonates: the group —S(O)2OR, wherein R is selected from among: hydrogen; C1-C6 alkyl; phenyl; C1-C6-alkyl-C6H5; Li; Na; K; Cs; Mg; and Ca.

Sulfates: the group —OS(O)2OR, wherein R is selected from among: hydrogen; C1-C6 alkyl; phenyl; C1-C6-alkyl-C6H5; Li; Na; K; Cs; Mg; and Ca.

Sulfones: the group —S(O)2R, wherein R is selected from among: hydrogen; C1-C6 alkyl; phenyl; C1-C6-alkyl-C6H5, and amines (to give sulfonamide) selected from the group: —NR'2, wherein each R' is independently selected from among: hydrogen; C1-C6 alkyl; C1C6-alkyl-C6H5; and phenyl, wherein if both R' are C1-C6 alkyl, then both R' can form an —NC3 to NC5 heterocyclic ring, wherein the remaining alkyl chain forms an alkyl substituent on the heterocyclic ring.

Carboxylate: the group —C(O)OR, wherein R is selected from among: hydrogen; C1-C6 alkyl; phenyl; C1-C6-alkyl-C6H5; Li; Na; K; Cs; Mg; and Ca, Carbonyl: the group —C(O)R, wherein R is selected from among: hydrogen; C1-C6 alkyl; phenyl; C1-C6-alkyl-C6H5, and amines (to give amide) selected from the group: —NR'2, wherein each R' is independently selected from among: hydrogen; C1-C6 alkyl; C1-C6-alkyl-C6H5; and phenyl, wherein if both R' are C1-C6 alkyl, then both R' can form an —NC3 to NC5 heterocyclic ring, wherein the remaining alkyl chain forms an alkyl substituent on the heterocyclic ring.

Phosphonates: the group —P(O)(OR)2, wherein each R is independently selected from among: hydrogen; C1-C6 alkyl; phenyl; C1-C6-alkyl-C6H5; Li; Na; K; Cs; Mg; and Ca.

Phosphates: the group —OP(O)(OR)2, wherein each R is independently selected from among: hydrogen; C1-C6 alkyl; phenyl; C1-C6-alkyl-C6H5; Li; Na; K; Cs; Mg; and Ca, Phosphines: the group —P(R)2, wherein each R is independently selected from among: hydrogen; C1-C6 alkyl; phenyl; and C1-C6-alkyl-C6H5, Phosphine oxide: the group —P(O)R2, wherein R is independently selected from among: hydrogen; C1-C6 alkyl; phenyl; and C1-C6-alkyl-C6H5; and amine (to give phosphonamidates), selected from the group: —NR'2, wherein each R' is independently selected from among: hydrogen; C1-C6-alkyl; C1-C6-alkyl-C6H5; and phenyl, wherein if both R' C1-C6 are alkyl, then both R' can form an —NC3 to NC5 heterocyclic ring, wherein the remaining alkyl chain forms an alkyl substituent on the heterocyclic ring.

Polyether: selected from the group comprising —(O—CH2-CH(R))$_n$—OH and —(O—CH2-CH(R))$_n$—H, wherein R is independently selected from among: hydrogen, alkyl, halogen, and n is from 1 to 250.

Silylalkyl: the group —SiR$_3$, wherein each R' is selected independently from among: hydrogen; C1-C6-alkyl; phenyl; C1-C6-alkyl-C6H5 and amine (to give sulfonamide) selected from the group: —NR'2, wherein each R' is selected independently from among: hydrogen; C1-C6-alkyl; C1C6-alkyl-C6H5; and phenyl, wherein if both R' C1-C6 are alkyl, then both R' can form an —NC3 to NC5 heterocyclic ring, wherein the remaining alkyl chain forms an alkyl substituent on the heterocyclic ring.

Silylalkyloxy: the group —OSiR$_3$, wherein each R is selected independently from among: hydrogen; C1-C6-alkyl; phenyl; C1-C6-alkyl-C6H5 and amine (to give sulfonamide) selected from the group: —NR'2, wherein each R' is selected independently from among: hydrogen; C1-C6-alkyl; C1C6-alkyl-C6H5; and phenyl, wherein if both R' are C1-C6 alkyl, then both R' can form a —NC3 to NC5 heterocyclic ring, wherein the remaining alkyl chain forms an alkyl substituent on the heterocyclic ring.

Unless otherwise specified, the following groups are more preferred groups within the general group definition:

Alkyl: linear and branched C1-C6 alkyl,

Long-chain alkyls: linear and branched C5-C10 alkyl, preferably C6-C8 alkyls

Alkenyl: C3-C6 alkenyl,

Cycloalkyl: C6-C8 cycloalkyl,

Alkoxy: C1-C4 alkoxy,

Long-chain alkoxy: linear and branched C5-C10 alkoxy, preferably linear C6-C8 alkoxy.

Alkylenes: selected from the group comprising: methylenes; 1,2-ethylenes; 1,3-propylenes; butane-2-ol-1,4-diyl; 1,4-butylenes; cyclohexane-1,1-diyl; cyclohexane-1,2-diyl; cyclohexane-1,4-diyl; cyclopentane-1,1-diyl; and cyclopentane-1,2-diyl, Aryl: selected from the group comprising: phenyl; biphenyl; naphthalenyl; anthracenyl; and phenanthrenyl, Arylenes: selected from the group comprising: 1,2-phenylenes; 1,3-phenylenes; 1,4-phenylenes; 1,2-naphthalenylenes; 1,4-naphthalenylenes; 2,3-naphthalenylenes, and 1-hydroxy-2,6-phenylenes, Heteroaryl: selected from the group comprising: pyridinyl; pyrimidinyl; chinoninyl; pyrazolyl; triazolyl; isoquinoninyl; imidazolyl; and oxazolidinyl, wherein the heteroaryl can be bonded to the compound via any atom in the ring of the selected heteroaryl, Heteroarylenes: selected from the group comprising: pyridine-2,3-diyl; pyridine-2,4-diyl; pyridine-2,6-diyl; pyridine- 3,5-diyl; quinoline-2,3-diyl; quinoline-2,4-diyl; isoquinoline-1,3-diyl; isoquinoline-1,4-diyl; Pyrazole-3,5-diyl; and imidazole-2,4-diyl, Heterocycloalkyl: selected from the group comprising: pyrrolidinyl; morpholinyl; piperidinyl; piperidinyl; 1,4-piperazinyl; tetrahydrofuranyl; 1,4,7-triazacyclononanyl; 1,4,8,11-tetraazacyclotetradecanyl; 1,4,7,10,13-pentaazacyclopentadecanyl; 1,4,7,10-tetraazacyclododecanyl; and piperazinyl, wherein the heteroaryl can be bonded to the compound via any atom in the ring of the selected heteroaryl.

Heterocycloalkylenes: selected from the group comprising: piperidin-2,6-ylenes; piperidin-4,4-ylidenes; 1,4-piperazin-1,4-ylenes; 1,4-piperazin-2,3-ylenes; 1,4-piperazin-2,6-ylenes; tetrahydrothiophen-2,5-ylenes; tetrahydrothiophen-3,4-ylenes; tetrahydrofuran-2,5-ylenes; tetrahydrofuran-3,4-ylenes; pyrrolidin-2,5-ylenes; pyrrolidin-2,2-ylidene; 1,4,7-triazacyclonon-1,4-ylenes; 1,4,7-triazacyclonon-2,3-ylenes; 1,4,7-triazacyclonon-2,2-ylidenes; 1,4,8,11-tetraazacyclotetradec-1,4-ylenes; 1,4,8,11-tetraazacyclotetradec-1,8-ylenes; 1,4,8,11-tetraazacyclotetradec-2,3-ylenes; 1,4,8,11-tetraazacyclotetradec-2,2-ylidenes; 1,4,7,10-tetraazacyclododec-1,4-ylenes; 1,4,7,10-tetraazacyclododec-1,7-ylenes; 1,4,7,10-tetraazacyclododec-2,3-ylenes; 1,4,7,10-tetraazacyclododec-2,2-ylidenes; 1,4,7,10,13-pentaazacyclopentadec-1,4-ylenes; 1,4,7,10,13-pentaazacyclopentadec-1,7-ylenes; 1,4-diaza-7-thia-cyclonon-1,4 ylenes; 1,4-diaza-7-thia-cyclonon-2,3-ylenes; 1,4-diaza-7-thiein cyclonon-2,2-ylidenes; 1,4-diaza-7-oxa-cyclonon-1,4-ylenes; 1,4 diaza-7-oxa-cyclonon-2,3-ylenes; 1,4-diaza-7-oxa-cyclonon-2,2-ylidenes; 1,4-dioxan-2,6-ylenes; 1,4-dioxan-2,2-ylidenes; tetrahydropyran-2,6-ylenes; tetrahydropyran-2,5-ylenes; and tetrahydropyran-2,2-ylidenes, an —C1-C6-alkyl-heterocycloalkyl, wherein the heterocycloalkyl is selected from the group comprised of: piperidinyl; 1,4-piperazinyl; tetrahydrofuranyl; 1,4,7-triazacyclononanyl; 1,4,8,11-tetraazacyclotetradecanyl; 1,4,7,10,13-pentaazacyclopentadecanyl; 1,4,7,10-tetraazacyclododecanyl; and pyrrolidinyl, wherein the heterocycloalkyl can be bonded to the compound via any atom in the ring of the selected heterocyloalkyl.

Amines: the group —N(R)2, wherein each R is independently selected from among: hydrogen; C1-C6-alkyl; and benzyl, Halogen: selected from the group comprising: F and Cl, Sulfonates: the group —S(O)2OR, wherein R is selected from among: hydrogen; C1-C6-alkyl; Na; K; Mg; and Ca, Sulfates: the group —OS(O)2OR, wherein R is selected from among: hydrogen; C1-C6-alkyl; Na; K; Mg; and Ca, Sulfones: the group —S(O)2R, wherein R is selected from among: hydrogen; C1-C6-alkyl; benzyl and amines selected from the group: —NR'2, wherein each R' is selected independently from among: hydrogen; C1-C6-alkyl; and benzyl, Carboxylate: the group —C(O)OR, wherein R is selected from among hydrogen; Na; K; Mg; Ca; C1-C6-alkyl; and benzyl, Carbonyl: the group: —C(O)R, wherein R is selected from among: hydrogen; C1-C6-alkyl; benzyl and amines selected from the group: —NR'2, wherein each R' is selected independently from among: hydrogen; C1-C6-alkyl; and benzyl, Phosphonates: the group —P(O) (OR)2, wherein each R is independently selected from among: hydrogen; C1-C6-alkyl; benzyl; Na; K; Mg; and Ca, Phosphates: the group —OP(O) (OR)2, wherein each R is independently selected from among: hydrogen; C1-C6-alkyl; benzyl; Na; K; Mg; and Ca, Phosphines: the group —P(R)2, wherein each R is independently selected from among: hydrogen; C1-C6-alkyl; and benzyl, Phosphine oxide: the group —P(O)R2, wherein R is independently selected from among: hydrogen; C1-C6-alkyl; benzyl and amines selected from the group: —NR'2, wherein each R' is selected independently from among: hydrogen; C1-C6-alkyl; and benzyl.

Polyether: selected from the group comprising —(O—CH$_2$—CH(R))$_n$—OH and —(O—CH$_2$—CH(R))$_n$—H wherein R is independently selected from among: hydrogen, methyl, halogen and n is from 5 to 50, preferably 10 to 25.

M, M$_n$ (n is a whole number): metals, wherein two metals M are selected independently of each other, unless otherwise indicated.

Enamines having the following structure are preferably used:

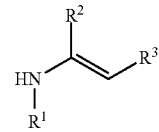

wherein R$^1$ and R$^2$ are as described above, but R$^3$ comprises an electron-attracting group, that is, it is selected from the group including formyl, carboxyl and/or carbonyl derivatives, keto, ketoaryl, halogen ketoaryl, ketoheteroaryl, ketoalkyl, halogen ketoalkyl, ketoalkenyl, halogen ketoalkenyl, phosphoalkyl, phosphonates, phosphates, phosphine, phosphine oxide, phosphoryl, phosphoaryl, sulfonyl, sulfoalkyl, sulfoarenyl, sulfonates, sulfates, sulfones, amines, polyether, silylalkyl, silylalkyloxy, wherein, one or more non-neighboring CH$_2$ groups can be substituted, independently from one another, by means of —O—, —S—, —NH—, —NR°—, —SiR°R°°—, —CO—, —COO—, —OCO—, —OCO—O—, —SO$_2$—, —S—CO—, —CO—S—, —CY1=CY2 or —C≡C— in suitable radicals, and specifically in such a way that the O and/or S atoms are not directly bonded to each other, likewise optionally replaced with aryl or heteroaryl, preferably including 1 to 30 C atoms (terminal CH$_3$-groups are understood as CH$_2$-groups in the sense of CH$_2$—H).

Compounds of this type have shown to be particularly advantageous in practice, because on the one hand, the Enamines obtained in this way are usually much more stable, and on the other hand, the reactivity is often greater.

It should be noted at this point that the Enamines according to the invention are either used in substance or produced in situ during the conversion, depending on the embodiment. This can take place (depending on the embodiment) by converting suitable amines with ketones (if required using dehydrating substances, such as for instance TiCl$_4$), or (if the Enamine with the above structure is utilized with an electron-attracting group) by means of Michael addition of amine to alkyne.

At this point it should also be noted that if nitriles are selected as N-containing carboxylic acid derivatives, they can either be used in substance or can be obtained in situ from other carboxylic acid derivatives or suitable precursor substances during the reaction. Suitable precursor substances are in particular those that produce nitriles under dehydrating conditions. In this case, if desired, the Enamine as well as the nitrile can be produced in situ during the process.

As described, the conversion is carried out in the presence of copper ions. Particularly preferable are copper(II) salts. In the event that an oxidizing agent is also present, in addition to the copper ions (see below), the preferred quantity ranges are ≥1% to ≤20%, more preferably ≥2% to ≤10% (with reference to the Enamine in mol/mol, before the beginning of the reaction).

According to one preferred embodiment, the oxidizing agent is selected from the group comprising oxygen (or air), ozone, hypohalogenides, in particular hypochlorite, peroxides, metals or metallic salts, or mixtures thereof Particularly preferred are metallic salts, especially Cu(II) salts, preferably Cu(OAc)$_2$ or Cu(OAc)$_2$ hydrate.

The oxidizing agent is preferably used in a ratio (with reference to the Enamine) of ≥1.5:1 to ≤30:1 (mol oxidizing agent:mol Enamine), even more preferably in a ratio of ≥2:1 to ≤10:1, and most preferably ≥2.5:1 to ≤3:1

The use of Cu(II) salts is particularly preferred, in particular for the reason that the copper can simultaneously act as a Lewis acid and will thus have an oxidizing as well as a catalytic effect. It is therefore preferred that the conversion be carried out in the presence of Cu(II) salts, and that the ratio of Enamine to Cu(II) salt ranges from ≥1.5:1 to ≤30:1 (mol Cu(II) salt:mol Enamine, before the reaction begins).

However, the invention is not limited to this; an oxidizing agent can just as well be used in addition to the copper ions.

As described, the reaction takes place in the presence of 2-picolinic acid (derivatives). "2-picolinic acid (derivatives)" are understood as 2-picolinic acid itself, as well as alkyl and halogen derivatives of 2-picolinic acid, or as the case may be mixtures of these compounds.

The ratio of 2-picolinic acid (derivatives) to Enamine (before the reaction begins) preferably ranges from ≥0.01% to ≤10% (mol/mol), more preferably from ≥0.05% to ≤8%, and most preferably from ≥1% to ≤5%.

Without being limited to this, it is presumed that the copper, with the 2-picolinic acid and the Enamine, forms a chelate complex, on which the nitrile accumulates. If applicable, the Pyrazole is then formed in an (at least formally) redox reaction during reduction of the copper. The copper is then oxidized again, if copper is used sub-stoichiometrically, so that a new reaction cycle can take place. The 2-picolinic acid is particularly advantageous for the formation of this complex, for steric and electronic reasons.

If oxygen (or air) is used as an oxidizing agent, it has been shown in practice that yields can be increased again by the addition of a carboxylic acid that is tertiary or secondary in α-position, in addition to the 2-picolinic acid. This is consequently a preferred embodiment of the invention. Here, α-tertiary carboxylic acids are preferred, such as pivalic acid. Here, the concentration (in mol % with reference to mol of copper ions) preferably amounts to >0% to 100%, preferably ≥30% to ≤70%, even more preferably ≥40% to ≤60%, as well as most preferably approximately 50%.

The aforementioned components, as well as those claimed and described in the sample embodiments to be used in accordance with the invention, are not subject to any special exceptions with regard to their size, shape, material selection, and technical concept, so that the selection criteria known in the field of application can be applied without restrictions.

Other details, features, and advantages of the subject matter of the invention can be seen in the dependent claims and in the subsequent description of the relevant examples, in which several exemplary embodiments of the inventive process are presented. These should be seen as purely illustrative in character.

General Experimental Regulation

Enamine starter material (0.25 mmol) and Cu(OAc)$_2$ (0.025 mmol, 10 Mol-%) was weighed into an oven-dried Schlenk flask (with a volume of 10 mL) which is provided with a magnetic stirrer, after which there was the addition of DCE (1,2-dichlorethane) (0.5 M), the nitrile (3.0 equiv.), and the 2-picolinic acid (0.0125 mmol, 5 Mol-%). Then the reaction mixture was vigorously stirred; the flask was briefly evacuated and then immediately filled with oxygen, this procedure (evacuation/filling) then being repeated two more times. The flask was then sealed and the reaction mixture stirred in a preheated oil bath at 110° C. for 24 hours. After cooling to room temperature (duration approx. 15 minutes), the reaction mixture was analyzed by means of ESI-MS, GC-MS and thin-layer chromatography. For the purpose of isolation, the reaction mixture was diluted with EtOAc (10 mL) and stirred briefly at room temperature. It was then filtered through three thin layers (sea sand (0.5 cm), celite (1.0 cm), sea sand (0.5 cm); previously moistened with EtOAc. The remaining residue was thoroughly washed with EtOAc (4×10 mL) and the combined filtrates were concentrated in a vacuum. The raw product was dissolved in CH$_2$Cl$_2$, adsorbed on silica, and purified via column chromatography (silica, gradient of pentane/EtOAc mixtures, if not otherwise stated).

Comparison Tests

In order to compare the effectiveness of 2-picolinic acid with that of other auxiliary substances, a series of tests was carried out, in accordance with the above experimental regulation, by means of the following reaction.

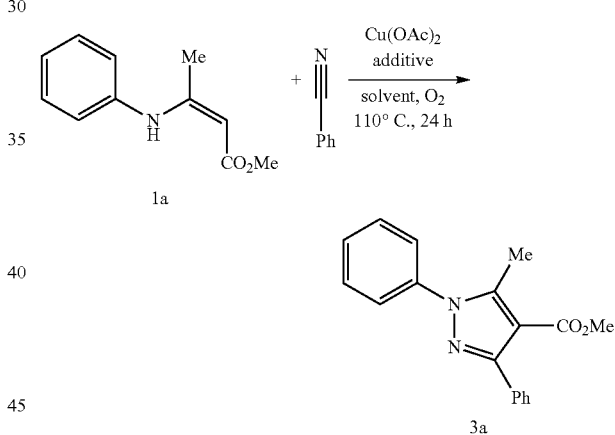

The following reaction conditions were specified: 0.25 mmol Enamine educt, Cu(OAc)$_2$ (10 Mol-%), PhCN (proportion, see table), additive, DCE (0.5 M), 110° C., 24 h, under an O$_2$ atmosphere (1 bar, closed vessel).

The test results (yields determined by GC analysis with mesitylene as internal standard) are presented in the following table:

TABLE I

| Equiv. PhCN | Additive (equiv.) | Yield (%) |
|---|---|---|
| 1.5 | — | 22 |
| 1.5 | Pivalic acid (0.1) | 48 |
| 1.5 | ZnCl$_2$ (0.1) | 0 |
| 1.5 | Water (0.11) | 26 |
| 1.5 | Pivalamide (0.1) | 52 |
| 1.5 | Pivalamide (1.0) | 21 |
| 1.5 | L-valine (0.1) | 39 |
| 1.5 | Acetamide (0.1) | 37 |
| 1.5 | Benzamide (0.1) | 64 |

TABLE I-continued

| Equiv. PhCN | Additive (equiv.) | Yield (%) |
|---|---|---|
| 1.5 | N-Methylpivalamide (0.1) | 40 |
| 1.5 | N-tert-Butylpivalamide (0.1) | 54 |
| 1.5 | N-Phenylpivalamide (0.1) | 51 |
| 1.5 | N-Methoxypivalamide (0.1) | 65 |
| 1.5 | N-Pivaloyloxypivalamide (0.1) | 27 |
| 1.5 | 9H-4,5-Diazafluorene-9-on (0.1) | 28 |
| 1.5 | 2-Pyrrolidinone (0.1) | 53 |
| 1.5 | N-Methyl-2-pyrrolidinone (0.1) | 38 |
| 1.5 | N-Methoxy benzamide (0.1) | 28 |
| 1.5 | Oxazolidine-2-on (0.1) | 45 |
| 1.5 | Piperidine-2-on (0.1) | 52 |
| 1.5 | N-Methoxypivalamide (1.0) | 44 |
| 1.5 | N-Methoxypivalamide (0.5) | 48 |
| 1.5 | N-Methoxypivalamide (0.25) | 45 |
| 1.5 | N-Methoxypivalamide (0.05) | 67 |
| 1.5 | N-Methoxypivalamide (0.05) | 16 |
| 1.5 | N-Methoxypivalamide (0.05) | 32 |
| 3.0 | N-Methoxypivalamide (0.05) | 69 |
| 3.0 | N-Methoxypivalamide (0.05) | 35 |
| 3.0 | N-Pyridine-2-ylbenzamide (0.05) | 27 |
| 3.0 | 2-Acetamido-benzoic acid (0.05) | 69 |
| 3.0 | Pivalic acid (0.05) | 40 |
| 3.0 | 2-thiophene carboxylic acid (0.05) | 59 |
| 3.0 | Pyridine (0.05) | 39 |
| 3.0 | DIPEA (0.05) | 43 |
| 3.0 | Et$_3$N (0.05) | 35 |
| 3.0 | N-Methoxypicolinamide (0.05) | 23 |
| 3.0 | 1H-Imidazole-2-carboxylic acid (0.05) | 20 |
| 3.0 | 1H-Pyrazole-3-carboxylic acid (0.05) | 33 |
| 3.0 | DL-Proline (0.05) | 14 |
| 3.0 | 2-Picolinic acid (0.05) | 84 |

A greater yield is seen with the use of picolinic acid compared to the other additives.

In addition, the following Pyrazoles were synthesized, in each case according to the general experimental regulation:

Methyl 5-methyl-1,3-diphenyl-1H-Pyrazole-4-carboxylate

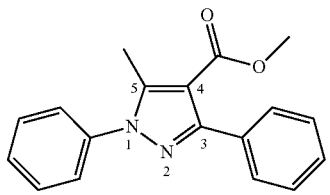 [SMILES: COC(=O)c1c(-c2ccccc2)nn(-c2ccccc2)c1C]

Yellowish solid.
Yield under reaction conditions: 49.6 mg, 0.17 mmol, 68%.
R$_f$(pentane/EtOAc 90:10): 0.21;
$^1$H NMR (300 MHz, CDCl3): δ=7.72-7.63 (m, 2H, H$_{arom}$), 7.56-7.35 (m, 8H, H$_{arom}$), 3.77 (s, 3H, CH$_3$), 2.59 (s, 3H, CH$_3$);
$^{13}$C NMR (75 MHz, CDCl3): δ=164.7 (CO), 153.7 (C$_{arom}$), 145.0 (C$_{arom}$), 138.8 (C$_{arom}$), 133.1 (C$_{arom}$), 129.4 (CH$_{arom}$), 129.3 (CH$_{arom}$), 128.8 (CH$_{arom}$), 128.4 (CH$_{arom}$), 127.8 (CH$_{arom}$), 125.9 (CH$_{arom}$), 110.4 (C$_{arom}$), 51.2 (CH$_3$), 12.9 (CH$_3$);
GC-MS: t$_R$ (50_20): 15.6 min;
EI-MS: m/z (%)=292 (100), 262 (21), 261 (100), 260 (22), 259 (20), 118 (15), 77 (52), 51 (14);
Exact Mass ESI-MS: calculated m/z for [C$_{18}$H$_{16}$N$_2$NaO$_2$]$^+$: 315.1104, found: 315.1095;
ATR-FTIR (cm$^{-1}$): 2948, 2406, 2236, 1712, 1595, 1529, 1500, 1453, 1428, 1382, 1327, 1307, 1246, 1183, 1148, 1088, 994, 770, 696, 655.

Methyl 5-methyl-1-phenyl-3-(m-tolyl)-1H-Pyrazole-4-carboxylate

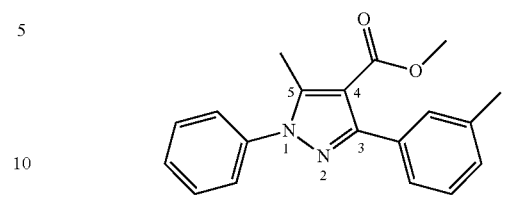

Yellowish solid
Yield under reaction conditions: 30.6 mg, 0.10 mmol, 40%.
R$_f$(pentane/EtOAc 90:10): 0.23;

Methyl 3-(4-ethoxyphenyl)-5-methyl-1-phenyl-1H-Pyrazole-4-carboxylate

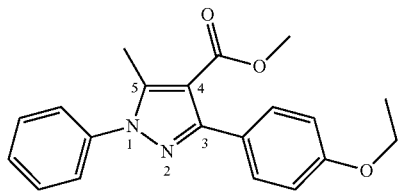 [SMILES: CCOc1ccc(-c2nn(-c3ccccc3)c(C)c2C(=O)OC)cc1]

Yellowish solid.
Yield under reaction conditions: 29.4 mg, 0.09 mmol, 35%.
R$_f$(pentane/EtOAc 90:10): 0.13;

Methyl 3-(4-(dimethylamino)phenyl)-5-methyl-1-phenyl-1H-Pyrazole-4-carboxylate

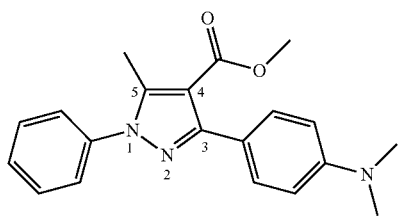 [SMILES: COC(=O)c1c(-c2ccc(N(C)C)cc2)nn(-c2ccccc2)c1C]

Yellow solid.
Yield under reaction conditions: 16.8 mg, 0.05 mmol, 20%.
R$_f$(pentane/EtOAc 90:10): 0.13;

Methyl 3-(4-acetylphenyl)-5-methyl-1-phenyl-1H-Pyrazole-4-carboxylate

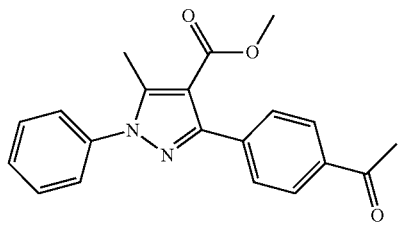 [SMILES: COC(=O)c1c(-c2ccc(C(C)=O)cc2)nn(-c2ccccc2)c1C]

Yellow solid
Yield under reaction conditions: 66.6 mg, 0.20 mmol, 80%
R$_f$(pentane/EtOAc 90:10): 0.04;

13

Methyl 5-methyl-1-phenyl-3-(3-(trifluoromethyl)phenyl)-1H-Pyrazole-4-carboxylate

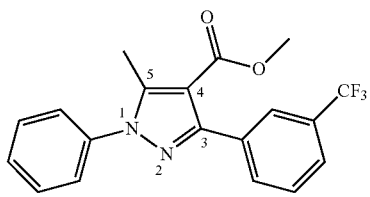 [SMILES: COC(=O)c1c(-c2cccc(C(F)(F)F)c2)nn(-c2ccccc2)c1C]

Yellow solid
Yield under reaction conditions: 69.9 mg, 0.19 mmol, 78%
$R_f$(pentane/EtOAc 90:10): 0.22;

Methyl 3-(2-fluorophenyl)-5-methyl-1-phenyl-1H-Pyrazole-4-carboxylate

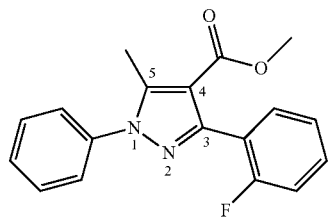 [SMILES: COC(=O)c1c(-c2ccccc2F)nn(-c2ccccc2)c1C]

Yellow solid
Yield under reaction conditions: 15.5 mg, 0.05 mmol, 20%
$R_f$(pentane/EtOAc 90:10): 0.19;

Methyl 3-(furan-2-yl)-5-methyl-1-phenyl-1H-pyrazol-4-carboxylate

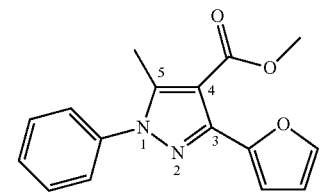 [SMILES: COC(=O)c1c(-c2ccco2)nn(-c2ccccc2)c1C]

Yellow solid
Yield under reaction conditions: 46.2 mg, 0.16 mmol, 66%
$R_f$(pentane/EtOAc 90:10): 0.15;

Methyl 3,5-dimethyl-1-phenyl-1H-Pyrazole-4-carboxylate

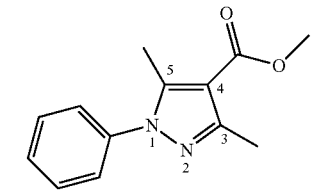 [SMILES: COC(=O)c1c(C)nn(-c2ccccc2)c1C]

Yellowish solid
Yield under reaction conditions: 17.4 mg, 0.08 mmol, 30%
$R_f$(pentane/EtOAc 90:10): 0.17;

14

Methyl 3-ethyl-5-methyl-1-phenyl-1H-Pyrazole-4-carboxylate

Yellow solid
Yield under reaction conditions: 19.5 mg, 0.08 mmol, 32%
$R_f$(pentane/EtOAc 90:10): 0.26;

Methyl 3-(4-fluorophenyl)-5-methyl-1-phenyl-1H-Pyrazole-4-carboxylate

White solid
Yield under reaction conditions: 54.3 mg, 0.17 mmol, 70%
$R_f$(pentane/EtOAc 90:10): 0.22;

Methyl 3-(4-fluorophenyl)-5-methyl-1-(o-tolyl)-1H-Pyrazole-4-carboxylate

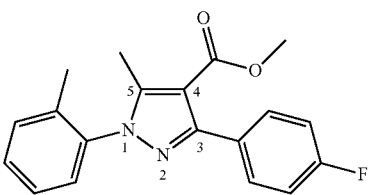 [SMILES: COC(=O)c1c(-c2ccc(F)cc2)nn(-c2ccccc2C)c1C]

Yellowish solid
Yield under reaction conditions: 54.3 mg, 0.17 mmol, 67%
$R_f$(pentane/EtOAc 90:10): 0.23;

Methyl 3-(4-fluorophenyl)-5-methyl-1-(m-tolyl)-1H-Pyrazole-4-carboxylate

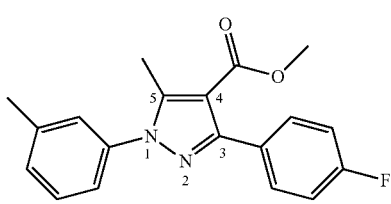 [SMILES: COC(=O)c1c(-c2ccc(F)cc2)nn(-c2cccc(C)c2)c1C]

Yellow solid
Yield under reaction conditions: 50.3 mg, 0.16 mmol, 62%
$R_f$(pentane/EtOAc 90:10): 0.23;

Methyl 3-(4-fluorophenyl)-5-methyl-1-(p-tolyl)-1H-Pyrazole-4-carboxylate

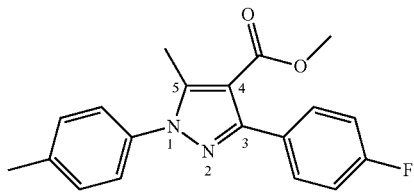 [SMILES: COC(=O)c1c(-c2ccc(F)cc2)nn(-c2ccc(C)cc2)c1C]

Yellow solid
Yield under reaction conditions: 55.8 mg, 0.17 mmol, 69%
$R_f$(pentane/EtOAc 90:10): 0.20;

Methyl 1-(4-ethoxyphenyl)-3-(4-fluorophenyl)-5-methyl-1H-Pyrazole-4-carboxylate

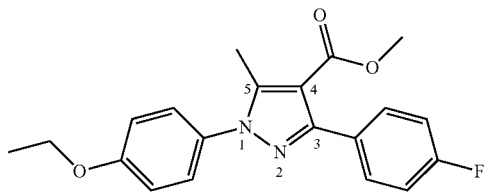 [SMILES: CCOc1ccc(-n2nc(-c3ccc(F)cc3)c(C(=O)OC)c2C)cc1]

Yellow solid
Yield under reaction conditions: 65.5 mg, 0.18 mmol, 74%
$R_f$(pentane/EtOAc 90:10): 0.17;

Methyl 1-(4-(dimethylamino)phenyl)-3-(4-fluorophenyl)-5-methyl-1H-Pyrazole-4-carboxylate

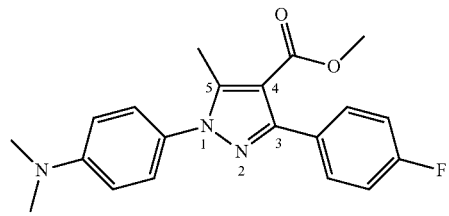 [SMILES: COC(=O)c1c(-c2ccc(F)cc2)nn(-c2ccc(N(C)C)cc2)c1C]

Yellow oil
Yield under reaction conditions: 13.2 mg, 0.04 mmol, 15%
$R_f$(pentane/EtOAc 90:10): 0.11;

Methyl 1,3-bis(4-fluorophenyl)-5-methyl-1H-Pyrazole-4-carboxylate

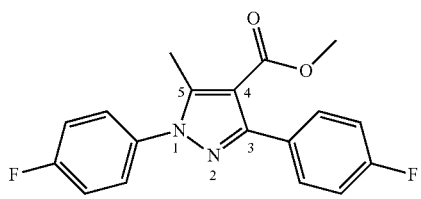 [SMILES: COC(=O)c1c(-c2ccc(F)cc2)nn(-c2ccc(F)cc2)c1C]

White solid
Yield under reaction conditions: 48.5 mg, 0.15 mmol, 59%
$R_f$(pentane/EtOAc 90:10): 0.22;

Methyl 1-(4-(ethoxycarbonyl)phenyl)-3-(4-fluorophenyl)-5-methyl-1H-Pyrazole-4-carboxylate

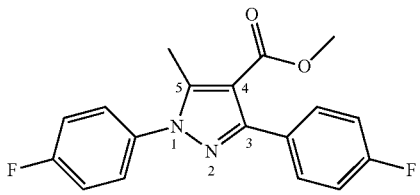 [SMILES: COC(=O)c1c(-c2ccc(F)cc2)nn(-c2ccc(F)cc2)c1C]

White solid
Yield under reaction conditions: 59.2 mg, 0.15 mmol, 62%
$R_f$(pentane/EtOAc 90:10): 0.13;

Methyl 3-(4-fluorophenyl)-5-methyl-1-(2-(trifluoromethyl)phenyl)-1H-Pyrazole-4-carboxylate (3s)

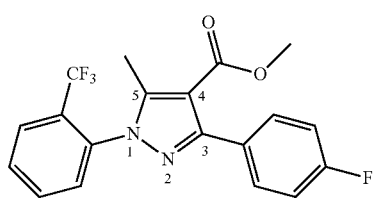 [SMILES: COC(=O)c1c(-c2ccc(F)cc2)nn(-c2ccccc2C(F)(F)F)c1C]

Yellow oil
Yield under reaction conditions: 46.5 mg, 0.12 mmol, 49%
$R_f$(pentane/EtOAc 90:10): 0.19;

Methyl 3-(3-fluorophenyl)-5-methyl-1-(4-(trifluoromethyl)phenyl)-1H-Pyrazole-4-carboxylate (3t)

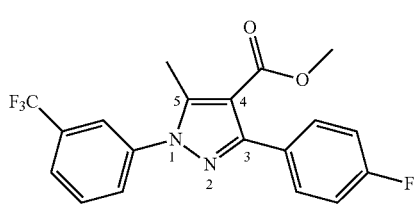 [SMILES: COC(=O)c1c(-c2ccc(F)cc2)nn(-c2cccc(C(F)(F)F)c2)c1C]

White solid
Yield under reaction conditions: 56.8 mg, 0.15 mmol, 60%
$R_f$(pentane/EtOAc 90:10): 0.20;

Methyl 3-(4-fluorophenyl)-5-methyl-1-(4-(trifluoromethyl)phenyl)-1H-Pyrazole-4-carboxylate (3u)

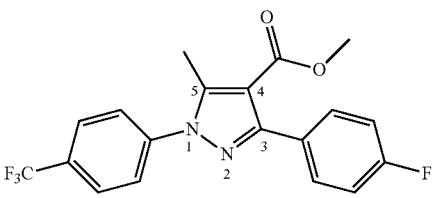 [SMILES: COC(=O)c1c(-c2ccc(F)cc2)nn(-c2ccc(C(F)(F)F)cc2)c1C]

Yellowish solid
Yield under reaction conditions: 53.9 mg, 0.14 mmol, 57%
$R_f$(pentane/EtOAc 90:10): 0.19;

Methyl 3-(4-fluorophenyl)-1,5-dimethyl-1H-Pyrazole-4-carboxylate (3v)

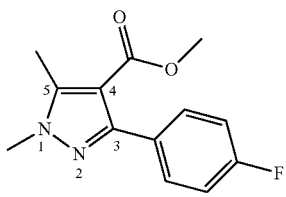 [SMILES: COC(=O)c1c(-c2ccc(F)cc2)nn(C)c1C]

White solid
Yield under reaction conditions: 26.1 mg, 0.11 mmol, 42%
R$_f$(pentane/EtOAc 90:10): 0.03;

Methyl 1-butyl-3-(4-fluorophenyl)-5-methyl-1H-Pyrazole-4-carboxylate

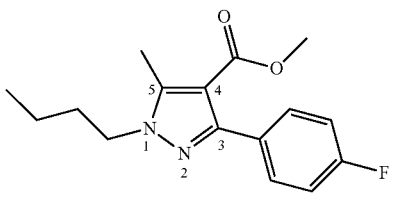 [SMILES: CCCCn1nc(-c2ccc(F)cc2)c(C(=O)OC)c1C]

Yellow oil
Yield under reaction conditions: 25.4 mg, 0.09 mmol, 35%
R$_f$(pentane/EtOAc 90:10): 0.19;

Ethyl 3-(4-fluorophenyl)-1-mesityl-5-methyl-1H-Pyrazole-4-carboxylate

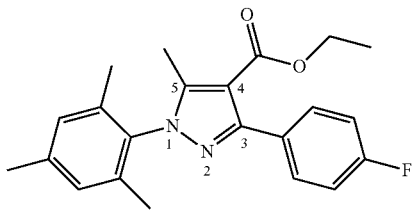 [SMILES: CCOC(=O)c1c(-c2ccc(F)cc2)nn(-c2c(C)cc(C)cc2C)c1C]

Yellowish solid
Yield under reaction conditions: 66.1 mg, 0.18 mmol, 72%
R$_f$(pentane/EtOAc 90:10): 0.46;

Ethyl 1-(2,6-diisopropylphenyl)-3-(4-fluorophenyl)-5-methyl-1H-Pyrazole-4-carboxylate

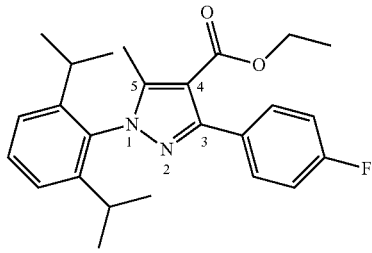 [SMILES: CCOC(=O)c1c(-c2ccc(F)cc2)nn(-c2c(C(C)C)cccc2C(C)C)c1C]

Yellowish solid
Yield under reaction conditions: 25.4 mg, 0.06 mmol, 25%
R$_f$(pentane/EtOAc 90:10): 0.53;

Ethyl 3-(4-fluorophenyl)-1,5-diphenyl-1H-Pyrazole-4-carboxylate

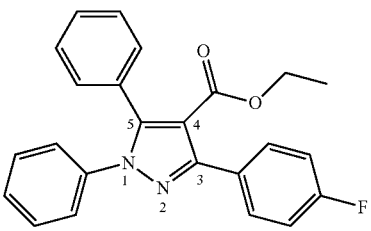 [SMILES: CCOC(=O)c1c(-c2ccc(F)cc2)nn(-c2ccccc2)c1-c1ccccc1]

Yellowish solid
Yield under reaction conditions: 64.5 mg, 0.17 mmol, 67%
R$_f$(pentane/EtOAc 90:10): 0.34;

(3-(4-fluorophenyl)-5-methyl-1-phenyl-1H-Pyrazole-4-yl)(phenyl)methanone

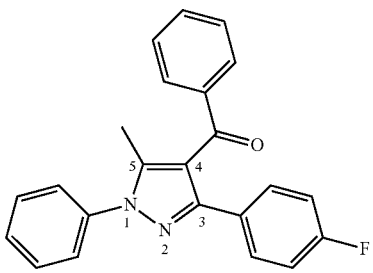 [SMILES: Cc1c(C(=O)c2ccccc2)c(-c2ccc(F)cc2)nn1-c1ccccc1]

White solid
Yield under reaction conditions: 16.1 mg, 0.05 mmol, 18%
R$_f$(pentane/EtOAc 90:10): 0.16;

The individual combinations of the components and the characteristics of the previously mentioned sample embodiments are exemplary in character; the replacement and substitution of these teachings with/by other teachings that are contained in this publication, with the cited publications, are also expressly taken into account. The person skilled in the art recognizes that variations, modifications, and other implementations described here may also appear without deviating from the inventive concept and the scope of the invention.

Correspondingly, the above description is to be considered exemplary rather than restrictive. The word include used in the claims does not exclude other components or steps. The indefinite article a/an does not exclude a plural meaning. The mere fact that certain dimensional units are cited in reciprocally different claims does not mean that a combination of these dimensional units cannot be advantageously utilized. The scope of the invention is defined in the following claims and in the corresponding equivalents.

The invention claimed is:

1. A method comprising:
producing Pyrazoles by means of a conversion of Enamines and nitriles in the presence of an oxidation agent, copper ions, and 2-picolinic acid (derivatives).

2. A method according to claim 1, wherein the conversion is carried out in the presence of Cu(II) salts, and a ratio of Enamine to Cu(II) salt ranges from ≥1.5:1 to ≤30:1 (mol Cu(II) salt:mol Enamine).

3. A method according to claim 1, wherein a ratio of 2-picolinic acid (derivatives) to Enamine ranges from ≥0.01% to ≤10% (mol/mol).

4. A method according to claim 1, wherein the conversion is carried out in the nitrile as a solvent.

5. A method according to claim 1, wherein a ratio of Enamine to nitrile ranges from ≥0.2:1 to ≤150:1 (mol nitrile:mol Enamine).

* * * * *

UNITED STATES PATENT AND TRADEMARK OFFICE
CERTIFICATE OF CORRECTION

PATENT NO. : 8,912,342 B2
APPLICATION NO. : 13/759107
DATED : December 16, 2014
INVENTOR(S) : Frank Glorius and Mamta Suri It is certified that error appears in the above-identified patent and that said Letters Patent is hereby corrected as shown below:

In the Specification

In Column 5, Line 49 delete the formula "C1C6-alkyl-C6H5" and insert the formula
--C1-C6-alkyl-C6H5.--

In Column 6, Line 25 delete the formula "C1C6-alkyl-C6H5" and insert the formula
--C1-C6-alkyl-C6H5.--

In Column 6, Line 34 delete the formula "C1C6-alkyl-C6H5" and insert the formula
--C1-C6-alkyl-C6H5.--

Signed and Sealed this
Twenty-eighth Day of July, 2015

Michelle K. Lee
*Director of the United States Patent and Trademark Office*